US011877751B2

(12) United States Patent
Jain et al.

(10) Patent No.: US 11,877,751 B2
(45) Date of Patent: Jan. 23, 2024

(54) METHODS AND DEVICES CONFIGURED TO PREVENT ASPIRATION

(71) Applicant: Emory University, Atlanta, GA (US)

(72) Inventors: Anand Jain, Decatur, GA (US); Nishani Kanthasamy, Johns Creek, GA (US); Ahmed Ali Alnamos, Watertown, MA (US); Oscar Gutierrez, Doraville, GA (US); Sondos Alnamos, Watertown, MA (US)

(73) Assignee: Emory University, Atlanta, GA (US)

( * ) Notice: Subject to any disclaimer, the term of this patent is extended or adjusted under 35 U.S.C. 154(b) by 511 days.

(21) Appl. No.: 17/007,443

(22) Filed: Aug. 31, 2020

(65) Prior Publication Data

US 2021/0059683 A1 Mar. 4, 2021

Related U.S. Application Data

(60) Provisional application No. 62/942,290, filed on Dec. 2, 2019, provisional application No. 62/893,602, filed on Aug. 29, 2019.

(51) Int. Cl.
*A61B 17/12* (2006.01)
*A61B 1/273* (2006.01)
(52) U.S. Cl.
CPC ...... *A61B 17/12099* (2013.01); *A61B 1/2736* (2013.01)
(58) Field of Classification Search
CPC ............ A61B 17/12099; A61B 1/2736; A61B 1/00082; A61B 1/00154; A61B 2017/00296; A61B 2017/00818; A61B 17/1204; A61B 17/12177
See application file for complete search history.

(56) References Cited

U.S. PATENT DOCUMENTS

| 3,397,669 | A |   | 8/1968 | Kohl |
|---|---|---|---|---|
| 4,464,175 | A | * | 8/1984 | Altman ............... A61M 3/0295 600/116 |
| 5,443,449 | A |   | 8/1995 | Buelna |
| 5,549,662 | A |   | 8/1996 | Fordenbacher |
| 5,556,413 | A |   | 9/1996 | Lam |
| 5,741,293 | A |   | 4/1998 | Wijay |
| 5,855,565 | A |   | 1/1999 | Bar-Cohen et al. |
| 7,276,075 | B1 |   | 10/2007 | Callas et al. |
| 7,914,574 | B2 |   | 3/2011 | Schmid et al. |

(Continued)

*Primary Examiner* — Tan-Uyen T Ho
*Assistant Examiner* — David P Stein
(74) *Attorney, Agent, or Firm* — Emory Patent Group

(57) ABSTRACT

The devices and methods can prevent pulmonary aspiration thereby allowing for procedures, such as an endoscopic procedure, to be performed under sedation without general anesthesia. The device may include a first end, a second end, and a length therebetween. The body may have a central lumen along the length. The device may include a first base member fixedly disposed at the first end and a second base member fixedly disposed at the second end. The device may also include an expandable assembly movable along the length of the body with respect to the first base member. The expandable assembly may be configured to move between a collapsed configuration and an expanded configuration. The expandable assembly may also be configured to expand radially with respect to the body when in the expanded configuration.

18 Claims, 5 Drawing Sheets

(56) References Cited

U.S. PATENT DOCUMENTS

| | | |
|---|---|---|
| 8,292,908 B2 | 10/2012 | Nieman et al. |
| 9,066,827 B2 | 1/2015 | Schmid et al. |
| 9,655,677 B2 | 5/2017 | Salahieh et al. |
| 9,707,071 B2 | 7/2017 | Sachar et al. |
| 9,839,539 B2 | 12/2017 | Agnew |
| 10,004,551 B2 | 6/2018 | Burnett |
| 10,660,771 B2 | 5/2020 | Giasolli et al. |
| 10,952,732 B2 | 3/2021 | Binmoeller et al. |
| 10,993,824 B2 * | 5/2021 | Longo .................... A61F 2/966 |
| 11,026,708 B2 | 6/2021 | Marks et al. |
| 2012/0283714 A1 * | 11/2012 | Mihalik ................. A61B 18/02 606/21 |
| 2015/0105809 A1 | 4/2015 | Connolly |

* cited by examiner

METHODS AND DEVICES CONFIGURED TO PREVENT ASPIRATION

CROSS-REFERENCE TO RELATED APPLICATIONS

This application claims the benefit of U.S. Provisional Application No. 62/893,602 filed Aug. 29, 2019 and U.S. Provisional Application No. 62/942,290 filed Dec. 2, 2019. The entirety of each of these applications is hereby incorporated by reference for all purposes.

BACKGROUND

Upper gastrointestinal (GI) endoscopic procedures are commonly performed to investigate, diagnose, and/or treat conditions affecting the upper part of the digestive system (esophagus, stomach, duodenum). During these procedures, an endoscope is threaded through the mouth and into the digestive system so that a clinician can diagnose and/or treat conditions of the upper part of the digestive system including the esophagus, stomach, and a upper portion of the small intestine (e.g., duodenum). Normally, this procedure is performed and/or attempted to be performed under sedation, for example, using propofol, without general anesthesia. However, this procedure has a risk of pulmonary aspiration from retained stomach or esophageal contents. This risk can be increased for those patients who have certain conditions (e.g., patients with gastroesophageal reflux disease who have an incompetent lower esophageal sphincter barrier). To reduce this risk initially or after finding retained contents during an upper GI endoscopic procedure performed under sedation without general anesthesia, the endoscopic GI procedure will generally be performed under general anesthesia; thereby increasing the risk of complications associated with the procedure as well as resource and financial costs.

SUMMARY

Thus, there is a need for devices and methods that can prevent pulmonary aspiration while allowing for an endoscopic procedure to be performed under sedation without general anesthesia.

This disclosure is directed to devices and methods that can allow for safe completion of procedures having a risk of aspiration under sedation without general anesthesia, even if the patient has retained stomach or esophageal contents. The devices and methods can prevent pulmonary aspiration, for example, during endoscopic procedures. Thus, by not requiring general anesthesia, procedures, such as endoscopic procedures, can be performed with a lower risk of complications using less healthcare resources at a lower healthcare cost.

In some embodiments, the device may include a body having a first end, a second end, and a length therebetween. The body may have a central lumen along the length. In some embodiments, the device may include a first base member fixedly disposed at the first end and having a first opening corresponding to the central lumen. The device may also include a second base member fixedly disposed at the second end and having a second opening corresponding to the central lumen. In some embodiments, the device may further include an expandable assembly movable along the length of the body with respect to the first base member. The expandable assembly may be configured to move between a collapsed configuration and an expanded configuration. The expandable assembly may be configured to expand radially with respect to the body when in the expanded configuration.

In some embodiments, the methods may include a method of occluding a lumen of a body. In some embodiments, the method may include providing a device having an expandable assembly in a collapsed configuration at a region of interest within a lumen. The method may also include causing one or more actuating members to pull an assembly hub member of the expandable assembly towards a first base member of the device to cause the expandable assembly to move to the expanded configuration to occlude the lumen.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
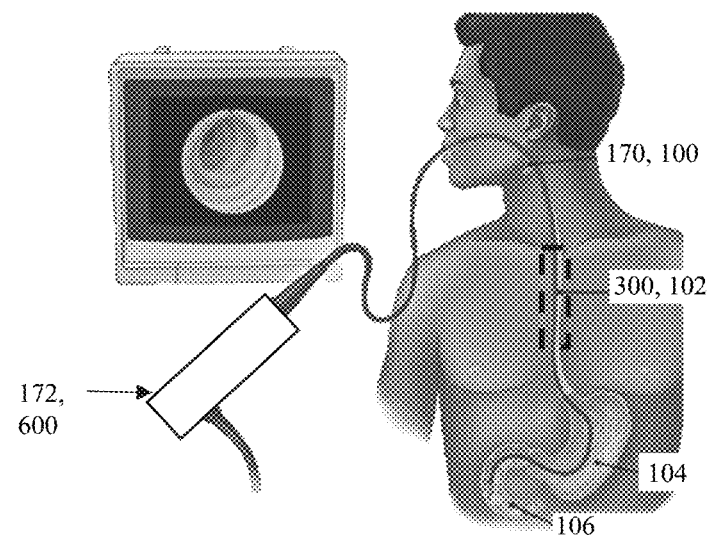
FIG. 1 shows an example of a device according to embodiments deployed in the esophagus over an endoscope advanced for a gastrointestinal procedure.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The devices and methods of the disclosure relate to devices that may be configured to be used alone and/or with an endoscope to prevent aspiration during procedures, such as endoscopic gastrointestinal procedures. For example, for an upper gastrointestinal procedure, the endoscopic procedure may be performed without general anesthesia, even for those patients considered high risk for aspiration. This can reduce the risks of complications, healthcare resources, costs, and time associated with performing procedures. For example, by allowing an endoscopic procedure to be performed without general anesthesia, the procedure may be performed using the device according to the disclosure in less resource intensive settings, such as in a clinical procedure room, emergency room, among others, or a combination thereof.

In some embodiments, the devices may include an expandable assembly that is configured to move between an expandable configuration and a collapsed configuration. In the expandable configuration, the expandable assembly may occlude the lumen in which it is delivered to prevent the outflow of contents, such as those in the stomach. For example, the expandable assembly can be configured to occlude the esophagus so as to reduce aspiration of the contents of the patient's stomach during a procedure such as gastrointestinal procedure.

In some embodiments, the device may be configured to be used alone and/or with another instrument, such as a gastrointestinal endoscope. The devices may be configured to be used with any gastrointestinal endoscope.

The devices and methods of the disclosure are described with respect to an upper gastrointestinal procedures. For example, the devices and methods can be configured to prevent aspiration so that a diagnostic or investigational procedure may be performed in the gastrointestinal region without the need of general anesthesia. However, it will be understood that the devices and methods are not limited to this type of procedure. The devices and methods may be used with an endoscope for any gastrointestinal procedure, with another instrument for a different procedure, by itself, or a combination thereof. For example, the devices and methods may also be used with an instrument for a procedure to be performed in any body lumen, such as, but not limited to a vessel or artery, for example, for a cardiac procedure. By way of another example, the device may be used alone to prevent aspiration during another procedure in a different region, for example, a colonoscopy.

Figure 2:
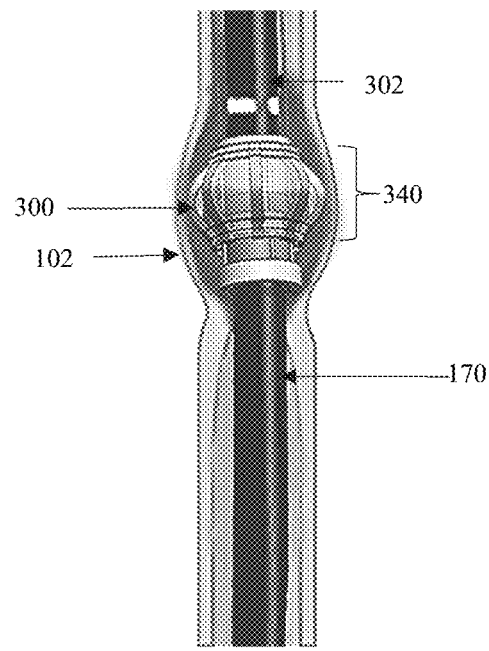
FIG. 2 shows an enlarged view of the deployed device shown in FIG. 1 according to embodiments.

FIGS. 1-6 shows an example of a device 300 according to some embodiments. FIGS. 1 and 2 show an example of the device 300 in which a flexible or the insertion tube 170 of an endoscope 100 (e.g., orally insertable scope), controlled by a controller 172, is advanced through the upper gastrointestinal region of a patient for a upper gastrointestinal procedure. In this example, the endoscope tube 170 may be advanced through the device 300 so that the tube 170 is disposed through the esophagus 102 and the stomach 104 and to the small intestine. As shown, the endoscope tube 170 may be advanced so that the endoscope tube 170 terminates at the duodenum 106.

As shown in FIGS. 1 and 2, the device 300 may be positioned along the esophagus so that its expandable assembly 340 may occlude the esophagus when it is in the expandable configuration, as shown in FIG. 2, to prevent aspiration of any contents of the stomach 104 and/or esophagus 102 during the upper gastrointestinal procedure.

Figure 3:
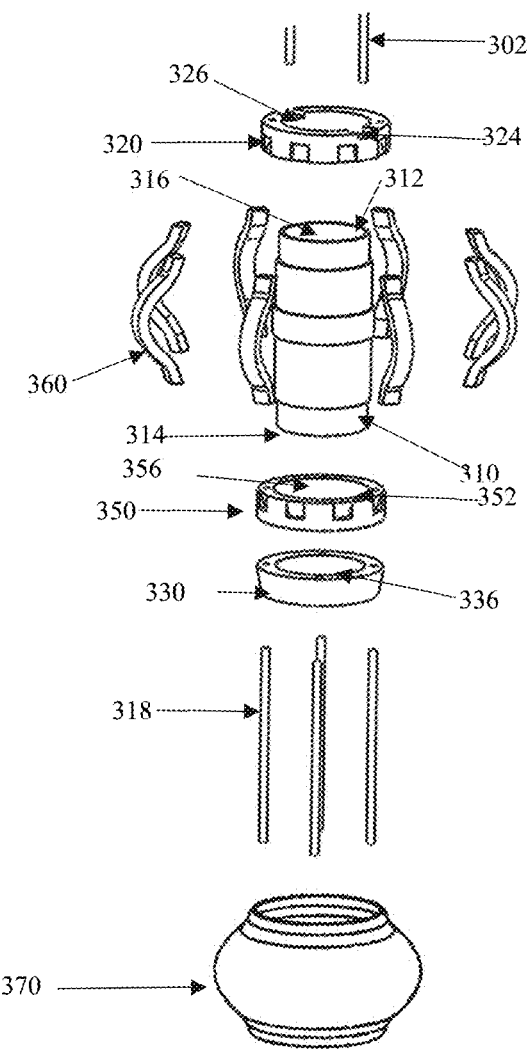
FIG. 3 shows an exploded view of the device according to embodiments.
Figure 4:
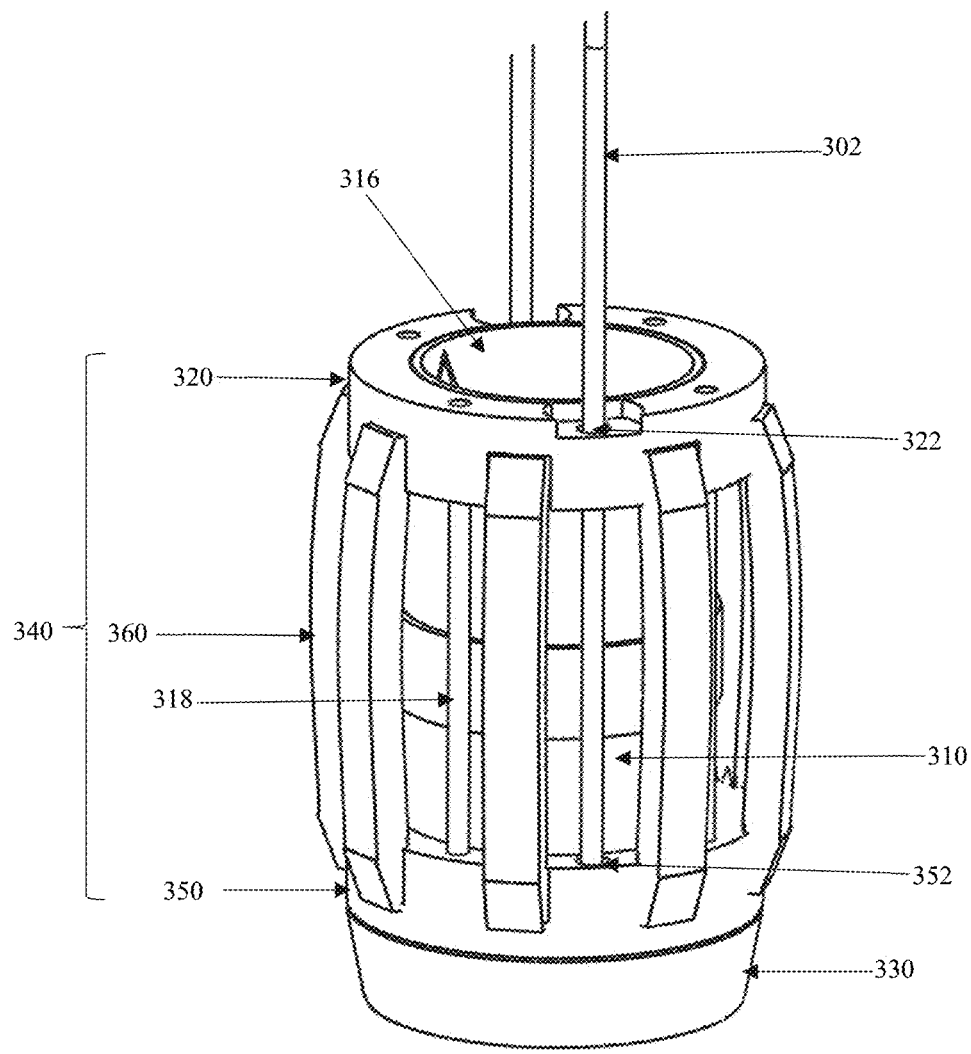
FIG. 4 shows the device in an closed configuration according to embodiments.

In some embodiments, the device 300 may be advanced when the expandable assembly 340 is in the collapsed configuration, as shown in FIG. 4. FIG. 3 shows an exploded view of the device 300. As shown in FIG. 3, the device 300 may include a body 310. In some embodiments, the body 310 may be configured to surround the sheath or tube of an instrument (e.g., endoscope tube 170). In some embodiments, the body 310 may have a first end 312, a second end 314, and a length therebetween.

In some embodiments, the body 310 may include a central lumen 316 disposed along the length. The central lumen 316 may be configured to receive and surround an insertable portion of an instrument, such as the endoscope tube 170. In some embodiments, the diameter of the central lumen 316 may be sized so that the instrument, e.g., endoscope tube 170, can advance/retract through to/from the desired (procedural) region.

In some embodiments, the body 310 may have a tubular shape. In other embodiments, the body 310 may have a different shape.

In some embodiments, the body 310 may be made of one or more biocompatible materials. For example, the one or more biocompatible materials may be rigid. By way of example, the one or more materials may include but is not limited to polybutylene succinate (PBS), polylactide (PLA), acrylonitrile butadiene styrene (ABS), resin, among others, or a combination thereof.

In some embodiments, the device 300 may include a first base member 320 fixedly disposed at the first end 312 and a second base member 330 fixedly disposed at the second end 314. In some embodiments each of the first base member 320 and the second base member 330 may have an opening 326, 336 that corresponds to the central lumen 316.

In some embodiments, the device 300 may include a cap (not shown) configured to be disposed on the second end 314/the second base member 330 so as to seal the opening 336. In other embodiments, at least second base member 330 may omit the opening 336 and be solid. This way, the device 300 may be configured to be used alone in the gastrointestinal region to prevent aspiration during a procedure being performed in another region (e.g., colonoscopy).

In some embodiments, the first base member 320 and the second base member 330 may have a ring shape. In some embodiments, the first base member 320 and the second base member 330 may have the same shape and/or dimensions as shown. In other embodiments, the first base member 320 and the second base member 330 may have different shape and/or dimensions.

Figure 5:
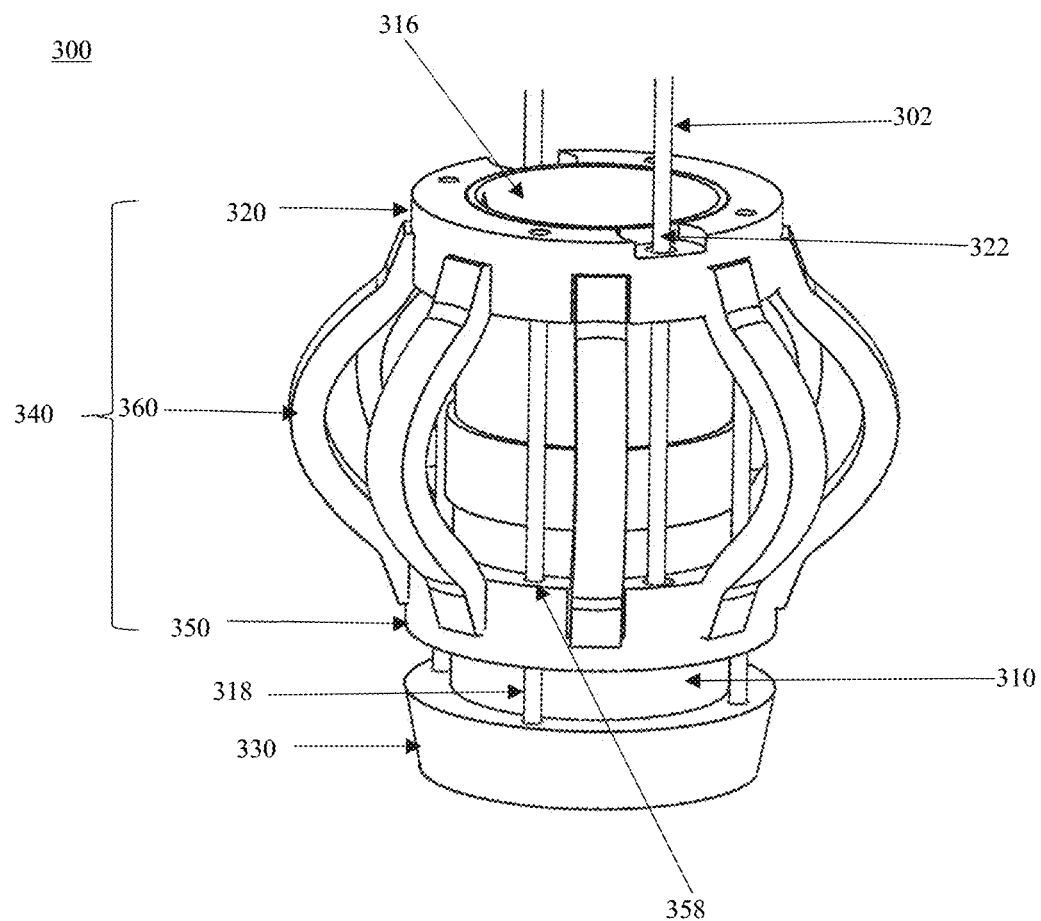
FIG. 5 shows the device in an expanded configuration according to embodiments.

In some embodiments, the device 300 may further include the expandable assembly 340 that is configured to move between a collapsed configuration and an expandable configuration. FIG. 4 shows the expandable assembly 340 in the collapsed configuration (without the covering member 370) and FIGS. 2 and 5 show the expandable assembly 340 in the expanded configuration (FIG. 5 shows the assembly 340 without the covering member 370).

In some embodiments, the expandable assembly 340 may include an assembly hub member 350 disposed along the length of the body 310 between the first base member 320 and the second base member 330. The assembly hub member 350 may be configured to slide along the length of the body 310 with respect to the first base member 320.

In some embodiments, the assembly hub member 350 may have an channel 356 so that the assembly hub member 350 may surround the body 310. In some embodiments, the assembly member 350 may have a ring shape. In some embodiments, the assembly hub member 350 may have the same diameter as the base members 320 and 330. In other embodiments, the assembly member 350 may have a different dimensions and/or shape.

In some embodiments, the expandable assembly 340 may further include a plurality of struts 360 configured to move between a collapsed configuration and an expanded configuration. In some embodiments, the plurality of struts may be disposed between and connected to the first base member 320 and the assembly hub member 350.

In some embodiments, the plurality of struts 360 may be longitudinally disposed with respect to the circumference of the body 310. In some embodiments, the plurality of struts 360 may be evenly spaced with respect to the circumference of the body 310. In some embodiments, the spacing may be different between the strut(s) 360. The plurality of struts 360 may include any number of struts and is not limited to the eight struts shown.

In some embodiments, the plurality of struts 360 may be configured to be elongated when the assembly hub member 350 is adjacent to the second base member 330 in the collapsed configuration as shown in FIG. 4. In some embodiments, the plurality of struts 360 may be configured to move to a radially extending, convex or curved shape from the elongated shape when the assembly hub member 350 is moved towards the first base member 320 to be in the expanded configuration, for example, as shown in FIGS. 2 and 5.

In some embodiments, the plurality of struts 360 may have a different configuration, shape, among others, or a combination thereof in the collapsed configuration and/or expanded configuration. For example, the plurality of struts 360 may be longitudinally, extending struts that have a curvilinear shape when in the expanded configuration. By way of another example, the plurality of struts 360 may be disposed sinusoidally/circumferentially in the collapsed and expanded configurations.

In some embodiments, the plurality of struts 360 may be made of a semi-flexible material. For example, plurality of struts 360 may be made of plastic, a shape memory material (e.g., Nitinol), metal, among others, or a combination thereof.

In some embodiments, the expandable assembly 340 may further include a covering member 370 configured to be disposed between the first base member 320 and the assembly hub member 350 so as to cover the plurality of struts 360. The covering member 370 may be configured to move between expanded and collapsed configurations based on the corresponding configuration the plurality of struts 360. For example, the covering member 370 may be configured to expand when the plurality of struts are in the expanded configuration as shown in FIG. 2 and to collapse in the collapsed configuration. For example, the covering member 370 may be similar to a balloon.

In some embodiments, the covering member 370 may be made of a flexible, biocompatible material. For example, the covering member 370 may be made of latex, silicone, polyethylene (e.g., microthin polyethylene), among others or a combination thereof.

In some embodiments, the device 300 may include one or actuating members 302 configured to move the expandable assembly 340 between the collapsed and expanded configurations. For example, the one or more actuating members 302 may be a pull wire, cable, among others, or a combination thereof. In some embodiments, the device 300 may include any number of one or more actuating members 302 and is not limited to the two actuating members 302 shown.

In some embodiments, the one or more actuating members 302 may be connected to the assembly member 340. In some embodiments, the first base member 320 may include one or more channels or through holes 326 through which the one or more actuating members 302 may be disposed. The number of one or more channels 326 may correspond to the number of one or more actuating members 302.

In some embodiments, the one or more actuating members 302 may be disposed external to the endoscope tube 170 as shown in FIG. 2. In some embodiments, the one or more actuating members 302 may include one or more markings to aid the clinician in proper placement of the device 300 during the procedure. The markings may include bands, dots, lettering, numbering, colors, other types of indicia, among others, or a combination thereof. The markings may indicate a predetermined or standardized width and/or spacing configured to indicate an insertion depth (e.g., position and/or distances of the device 300 with respect to anatomical structures (e.g., esophagus)).

In some embodiments, the device 300 may include a sheath that extends from the first base member 320. In some embodiments, the sheath may cover the one or more actuating members 302. For example, the sheath may include channels through which the one or more actuating members 302 may be disposed. In some embodiments, the sheath may include the one or more markings.

In some embodiments, the device 300 may optionally include one or more supporting members 318 fixedly disposed between and connecting the first base member 320 and the second base member 330. In some embodiments, the one or more support members 318 may be disposed so as to surround the body 310. The one or more support members 318 may be spaced, longitudinally elongated members.

In some embodiments, the one or more supporting members 318 may be a rod, wire, among others, or a combination thereof. In some embodiments, the device 300 may include any number of supporting members 318 and is not limited to the four supporting members shown.

In some embodiments, the assembly hub member 350 may include through holes or channels 358 through which the one or more support members 318 may be disposed between the first base member 320 and the second base member 330. The number of through holes or channels may correspond to the number of the one or more support members 318.

In some embodiments, the expandable assembly 340 may be configured to linearly slide along the one or more support members 318 with respect to the length of the body 310 when moving between the expanded and collapsed configurations. This way, the support members 318 may be configured to prevent and/or reduce radial rotation of the device when the expandable assembly linearly moves with respect to the length of the body 310 to expand and/or to collapse.

In some embodiments, the one or more support members 318 may have a different configuration, for example, configured to prevent and/or reduce radial rotation. For example, the one or more support members 318 may have a different dimensions (e.g., length). In some embodiments, the one or more support members 318 may be configured to act as a track on which the expandable assembly 340 may move linearly between expanded and collapsed configurations.

Figure 6:
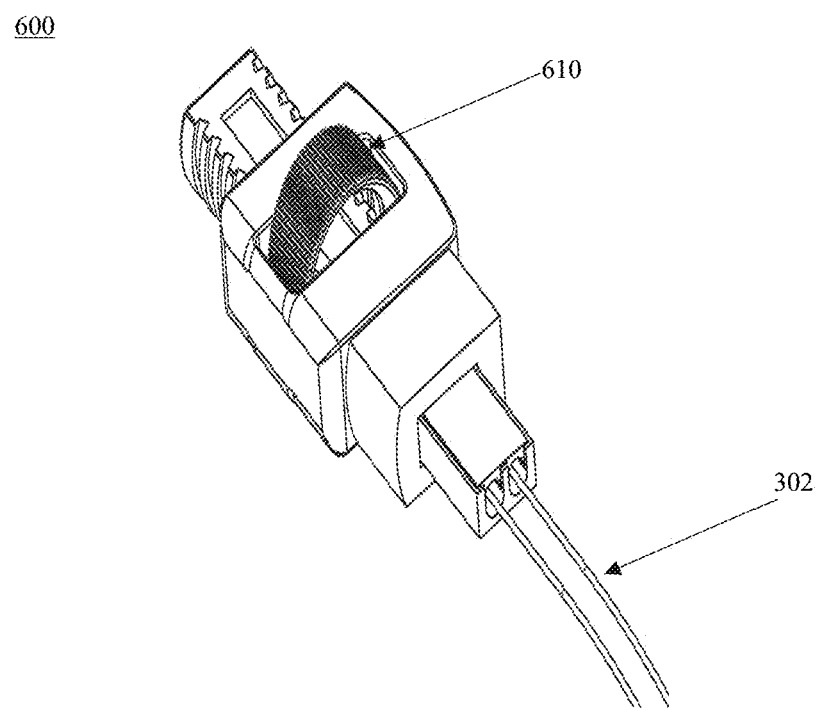
FIG. 6 shows an example of the control handle of the device according to embodiments.

In some embodiments, the device 300 may include a control handle 600 as shown in FIGS. 1 and 6. In some embodiments, the control handle 600 may be separate from the endoscope controller 172, integrated with the endoscope controller 172, among others, or a combination thereof.

In some embodiments, the control handle 600 may include an actuator 610 configured to control the pull and release of the one or more actuating members 302 so that the expandable assembly 340 is moved between the expanded and collapsed configurations. In some embodiments, the actuator 610 may be a rotating knob as shown in FIG. 6 so that the rotation of the knob results in the linear pull and release of all of the one or more actuating members 302. In some embodiments, the actuator 610 may have a different configuration.

In some embodiments, the control handle 600 may include markings on the handle 600 and/or on the actuator 610 to indicate the movement of the one or more actuating members 302 corresponding to the collapsed and expanded configurations. For example, the markings may indicate one or more amounts of tension or pull of the actuating member(s) 302 corresponding to a level of expansion.

For example, when using the device 300 for a procedure, the device 300 may be advanced with the expandable assembly 340 in the collapsed configuration as shown in FIG. 4. the endoscope tube 170. The device 300 may be advanced with a device (e.g., endoscope 170) or by itself.

By way of example, the device 300 may be disposed on the endoscope tube 170 before advancement and then may be advanced orally together (with the expandable assembly 340 in the collapsed configuration). In some embodiments, the clinician may advance the endoscope tube 170 and the device 300 until the markings on the device 300 (e.g., the one or more actuating members 302) indicate that the device 300 is disposed at the target region, e.g., in the esophageal region of a patient, for example, between T1 and T4. After the device 300 is at the target region (e.g., esophageal region), the clinician may use the handle 600 to move the expandable assembly 340 from the collapsed configuration as shown in FIG. 4 to the expanded configuration as shown in FIG. 5. By rotating the actuator 610, the one or more actuating members 302 may be pulled to cause the expandable assembly 340 to expand as shown in FIGS. 2 and 5.

By way of another example, the device 300 may be advanced orally with the expandable assembly 340 in the collapsed configuration to the target region e.g., in the esophageal region of a patient, for example, between T1 and T4. After the device 300 is at the target region (e.g., esophageal region), the clinician may use the handle 600 to move the expandable assembly 340 from the collapsed configuration as shown in FIG. 4 to the expanded configuration as shown in FIGS. 2 and 5. After the device 300 is moved to the expanded configuration, the procedure may be performed while the device 300 is in the expanded configuration. For example, for a gastrointestinal procedure, a clinician may advance an endoscope through the lumen 316 of the deployed device 300 to the desired region. In another example, if the device 300 includes at least a sealed second base member 330 (e.g., it is capped), the clinician may perform a procedure in another region (e.g., colonoscopy) while the device 300 is in the expanded configuration.

In some examples, as shown in FIG. 2, the clinician may actuate the actuator 610 so that the expandable assembly 340 expands to the expanded configuration such that the covering member 370 contacts the esophageal wall so that the esophagus can be occluded by the assembly 340 thereby preventing aspiration of any stomach/esophageal contents during the performance of the procedure (e.g., diagnostic and/or treatment endoscopic procedure). For example, the covering member 370 may be configured to expand to a diameter that contacts the esophageal wall so that the covering member 370 "retains contact (i.e., "hugs" the wall) with the esophageal wall, for example, during esophageal peristalsis, advancement/retraction of the endoscope tube 170 through the lumen 316, among others, or a combination thereof In some embodiments, the plurality of struts 170 may be configured for a maximum radial expansion of about 33 mm or less.

In some embodiments, the collapsed configuration of the device 300 may be the default configuration. For example, the controller 600 may be configured to release the one or more actuating members 302 so that the assembly 340 returns to the collapsed configuration if there is a failure during use.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed is:

1. A device, comprising:
   a body having a first end, a second end, and a length therebetween, the body having a central lumen along the length;
   a first base member fixedly disposed at the first end and having a first opening corresponding to the central lumen;
   a second base member fixedly disposed at the second end and having a second opening corresponding to the central lumen;
   an expandable assembly movable along the length of the body with respect to the first base member, the expandable assembly including:
      an assembly hub member disposed between the first base member and the second base member, the assembly hub member being movably disposed along the length of the body; and
      a plurality of struts (i) configured to move between the collapsed configuration and the expanded configuration and (ii) disposed between the first base member and the assembly hub member.
   the expandable assembly being configured to move between a collapsed configuration and an expanded configuration; and
   the expandable assembly being configured to expand radially with respect to the body when in the expanded configuration; and
   one or more supporting members disposed between the first base member and the second base member.

2. The device according to claim 1, wherein the plurality of struts are longitudinally disposed and radially spaced with respect to the body.

3. The device according to claim 2, wherein:
   the plurality of struts have an elongated shape when the expandable assembly is in the collapsed configuration; and
   the plurality of struts have a curved shape when the expandable assembly is in the expanded configuration.

4. The device according to claim 1, wherein the expandable assembly is configured to be in the collapsed configuration when the assembly hub member is adjacent to the second base member so that the plurality of struts are elongated and parallel to the body.

5. The device according to claim 4, wherein the expandable assembly is configured to be in the expanded configuration when the assembly hub member is moved closer to the first base member so that the plurality of struts radially extend from the body.

6. The device according to claim 1, further comprising:
   one or more actuating members connected to the assembly hub member; and
   the one or more actuating members being configured to linearly move the assembly hub member with respect to the body and the first base member to move the expandable assembly between the expanded configuration and the collapsed configuration.

7. The device according to claim 6, wherein the first base member includes one or more through holes, each actuating member being disposed through each through hole to the assembly hub member.

8. The device according to claim 6, further comprising:
one or more markings disposed on the one or more actuating members, the one or more markings indicating an insertion depth.

9. The device according to claim 6, further comprising:
a control handle including an actuator connected to the one or more actuating members,
wherein the actuator is configured to move the one or more actuating members so that the expandable assembly moves between the expanded configuration and the collapsed configuration.

10. The device according to claim 1, wherein:
the expandable assembly includes a covering member disposed between the first base member and the assembly hub member;
the covering member is disposed over the plurality of struts; and
the covering member is configured to move between the collapsed and expanded configurations corresponding to a configuration of the plurality of struts.

11. The device according to claim 1, wherein the expandable assembly is configured to move along the one or more supporting members to move between the collapsed and expanded configurations.

12. The device according to claim 1, wherein:
the central lumen is configured to receive an endoscope tube and sized so that the endoscope tube can advance/retract through the central lumen.

13. A method of occluding a lumen of a body, comprising:
providing a device having an expandable assembly in a collapsed configuration at a region of interest within a lumen, the device including:
a body having a first end, a second end, and a length therebetween, the body having a central lumen along the length;
a first base member fixedly disposed at the first end and having a first opening corresponding to the central lumen;
a second base member fixedly disposed at the second end and having a second opening corresponding to the central lumen;
the expandable assembly being movable along the length of the body with respect to the first base member, the expandable assembly including:
an assembly hub member disposed between the first base member and the second base member, the assembly hub member being movably disposed along the length of the body; and
a plurality of struts (i) configured to move between the collapsed configuration and the expanded configuration and (ii) disposed between the first base member and the assembly hub member;
the expandable assembly being configured to move between the collapsed configuration and an expanded configuration; and
the expandable assembly being configured to expand radially with respect to the body when in the expanded configuration: and
one or more supporting members disposed between the first base member and the second base member; and
causing one or more actuating members to pull the assembly hub member of the expandable assembly towards the first base member of the device to cause the expandable assembly to move to the expanded configuration to occlude the lumen.

14. The method according to claim 13, wherein the region of interest is the esophagus.

15. The method according to claim 13, further comprising:
advancing the device having the expandable assembly in the collapsed configuration with an endoscope tube orally until the device reaches an esophageal region;
advancing the endoscope when the expandable assembly is in the expandable configuration to perform a gastrointestinal procedure.

16. The method according to claim 13, further comprising:
advancing the device having the expandable assembly in the collapsed configuration until the device reaches an esophageal region; and
performing a procedure after the expanded assembly is moved to the expanded configuration.

17. The method according to claim 16, further comprising:
advancing an endoscope through the central lumen of the device when the expandable assembly is in the expanded configuration.

18. The method according to claim 13, wherein an actuator of a control handle of the device is actuated to move the one or more actuating members to cause the expandable assembly to move between the collapsed and expanded configurations.

* * * * *